(12) United States Patent
Song et al.

(10) Patent No.: US 9,018,373 B2
(45) Date of Patent: Apr. 28, 2015

(54) METHOD FOR PREPARING TEMSIROLIMUS

(71) Applicant: Tianjin Weijie Technology Co., Ltd., Tianjin (CN)

(72) Inventors: Honghai Song, Tianjin (CN); Long Tang, Tianjin (CN); Wei Chen, Tianjin (CN); Zheng Li, Tianjin (CN); Jinzhou Li, Tianjin (CN); Zhicun Sun, Tianjin (CN); Jiajin Feng, Tianjin (CN)

(73) Assignee: Tianjin Weijie Technology Co., Ltd., Tianjin (CN)

( * ) Notice: Subject to any disclaimer, the term of this patent is extended or adjusted under 35 U.S.C. 154(b) by 146 days.

(21) Appl. No.: 13/935,476

(22) Filed: Jul. 3, 2013

(65) Prior Publication Data

US 2013/0296572 A1 Nov. 7, 2013

Related U.S. Application Data

(63) Continuation-in-part of application No. PCT/CN2011/074080, filed on May 16, 2011.

(30) Foreign Application Priority Data

Jan. 7, 2011 (CN) .......................... 2011 1 0002893

(51) Int. Cl.
*C07D 498/00* (2006.01)
*C07D 498/18* (2006.01)

(52) U.S. Cl.
CPC .................................. *C07D 498/18* (2013.01)

(58) Field of Classification Search
CPC .................................................. C07D 498/18
USPC ........................................................ 540/456
See application file for complete search history.

(56) References Cited

U.S. PATENT DOCUMENTS

| | | | |
|---|---|---|---|
| 5,362,718 A | 11/1994 | Skotnicki et al. | |
| 8,524,893 B2 * | 9/2013 | Gupta et al. | 540/456 |
| 8,754,207 B2 * | 6/2014 | Dave et al. | 540/456 |
| 2005/0033046 A1 | 2/2005 | Chew et al. | |
| 2005/0234086 A1 | 10/2005 | Gu et al. | |

FOREIGN PATENT DOCUMENTS

| | | |
|---|---|---|
| CN | 1942477 A | 4/2007 |
| CN | 102020662 A | 4/2011 |

OTHER PUBLICATIONS

Li Wen-Long et al, Synthesis and characterization of star-shaped poly(κ-caprolactone) with end group folates. Journal of Functional Materials, 2010, pp. 222-224, vol. 41, No. 2, Journal of Functional Materials Editorial Office, Chongqing, CN.

Jean-D'Amour K. Twibanire et al, Synthesis of new cores and their use in the preparation of polyester dendrimers. Tetrahedron, 2010, pp. 9602-9609, vol. 66, No. 50, Pergamon Press, Oxford, GB.

Ulf Annby et al, Benzylidene protected bis-MPA., a convenient dendrimer building block, Tetrahedron Letters, 1998, pp. 3217-3220, vol. 39, Pergamon Press, Oxford, GB.

Thomas C. Bruice et al, A search for carboxyl-group catalysis in ketal hydrolysis, Journal of the American Chemical Society, 1967, pp. 3568-3576, vol. 89, No. 14, American Chemical Society, US.

* cited by examiner

*Primary Examiner* — John Mabry
(74) *Attorney, Agent, or Firm* — Matthias Scholl P.C.; Matthias Scholl

(57) ABSTRACT

A method for preparing temsirolimus, the method including: using a substituted aromatic aldehyde to protect 2,2-dimethylol propionic acid to produce intermediate II; carrying out reaction between the intermediate II and 2,4,6-trichlorobenzoyl chloride; carrying out condensation reaction between a resulting product and rapamycin to produce intermediate III; and finally using sulfuric acid to remove a protecting group from the intermediate III to yield temsirolimus.

4 Claims, 5 Drawing Sheets

METHOD FOR PREPARING TEMSIROLIMUS

CROSS-REFERENCE TO RELATED APPLICATIONS

This application is a continuation-in-part of International Patent Application No. PCT/CN2011/074080 with an international filing date of May 16, 2011, designating the United States, now pending, and further claims priority benefits to Chinese Patent Application No. 201110002893.X filed Jan. 7, 2011. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 14781 Memorial Drive, Suite 1319, Houston, Tex. 77079.

BACKGROUND OF THE INVENTION

1. Field of the Invention

The invention relates to the field of medical technology, and more particular to a method for synthesizing temsirolimus.

2. Description of the Related Art mTOR kinase is an important protein to control cell proliferation, growth, and survival. As a medicine for treating kidney cancers, temsirolimus is able to inhibit mTOR kinase, lower the level of some angiogenesis factors, such as the vascular endothelial growth factor, inhibit the growth of new vessels, and finally lead to the death of cancer cells.

A typical method for preparing temsirolimus is shown in FIG. 2. The method includes: carrying out reaction between 2,2-dimethylol propionic acid and 2,4,6-trichlorobenzoyl chloride under the protection of 2,2-dimethoxypropane to yield an anhydride; condensing the anhydride with rapamycin, separating intermediate A-1, and finally removing a protecting group to yield temsirolimus. However, the method has defects that it is difficult to separate a product from a by-product produced by synchronous esterification of 31- and 42-hydroxyls, and the total yield is only 20%.

An improved synthetic method is shown in FIG. 3. The method includes: protecting the 31- and 42-hydroxyls by trimethylchlorosilane; selectively removing a 42-protecting group to yield intermediate B-1; carrying out a condensation reaction between the intermediate B-1 and the anhydride; and finally removing a 32-protecting group to yield temsirolimus. Although the yield of the method is increased to 47%, the method has multiple reaction steps and a complicate process.

Further improvement is shown in FIG. 4, including: protecting 2,2-dimethylol propionic acid by phenylboronic acid, and removing the protecting group by 2-methyl-2,4-pentanediol to yield temsirolimus. And another improved method is shown in FIG. 5. The method includes: enzyme catalyzing rapamycin, carrying out reaction between 42-hydroxyl radical of rapamycin and alkyl group protected 2,2-dimethylol propionic acid, and removing the protecting group to yield temsirolimus. The method has high yield, but high production cost.

Thus, methods for synthesizing temsirolimus in the prior art are disadvantageous in low yield, multiple reaction steps, complicate process, and high production cost.

SUMMARY OF THE INVENTION

In view of the above-described problems, it is one objective of the invention to provide a method for preparing temsirolimus that has a simple process, low cost, and high efficiency.

To achieve the above objective, in accordance with one embodiment of the invention, there is provided a method for preparing a compound of formula I,

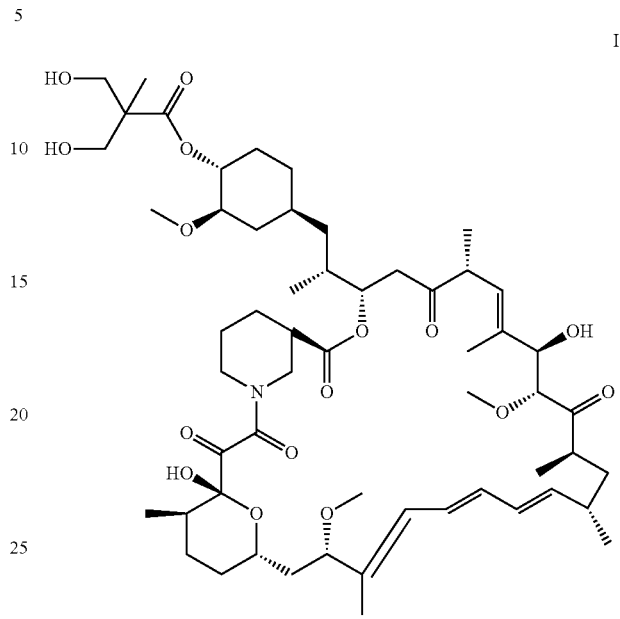

and the method comprises:

1) preparing a solution comprising: a raw material comprising 2,2-dimethylol propionic acid and a substituted aromatic aldehyde, a catalyst comprising p-toluenesulfonic acid, and a solvent comprising methylbenzene; heating and refluxing the solution for 8 h; precipitating a product; adding a saturated sodium carbonate aqueous solution and ether to the solution; allowing a resulting mixture to stand for stratification; separating an aqueous phase from an organic phase; adjusting pH value of the aqueous phase to be neutral; filtrating, and drying the aqueous phase to yield intermediate II represented by the following formula:

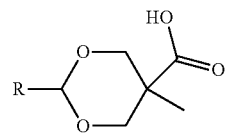

wherein, R represents

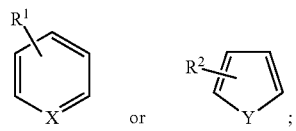

X represents a carbon atom or nitrogen atom; $R^1$ represents a hydrogen atom, between one and five $C_1$-$C_6$ alkyls, between one and five $C_1$-$C_6$ alkoxys, between one and five $C_1$-$C_6$ alkenyls, between one and five $C_1$-$C_6$ alkynyls, between one and five hydroxyls, one or two methylenedioxys ($OCH_2O$), one or two ethylenedioxys ($OCH_2CH_2O$), between one and five halogen atoms, between one and five nitryls, between one and five trifluoromethyls, or between one and five trifluoromethoxys; Y represents a nitrogen atom, oxygen atom, or sulfur atom; and $R^2$ represents a hydrogen atom, between one and four $C_1$-$C_6$ alkyls, between one and four $C_1$-$C_6$ alkoxys, between one and four $C_1$-$C_6$ alkenyls, between one and four $C_1$-$C_6$ alkynyls, between one and four hydroxyls, between one and four halogen atoms, between one and four nitryls, between one and four trifluoromethyls, or between one and four trifluoromethoxys;

2) dissolving the intermediate II, an alkali, and 2,4,6-trichlorobenzoyl chloride, in a first organic solvent to form a mixture; allowing the mixture to react in the presence of nitrogen gas at a temperature of between −20 and 40° C. for between 4 and 5 h; adjusting the temperature of the mixture to −10° C.; adding rapamycin and an acid binding agent to the mixture, allowing the mixture to react overnight at room temperature; and separating a product by silica gel column chromatography to yield intermediate III represented by the following formula:

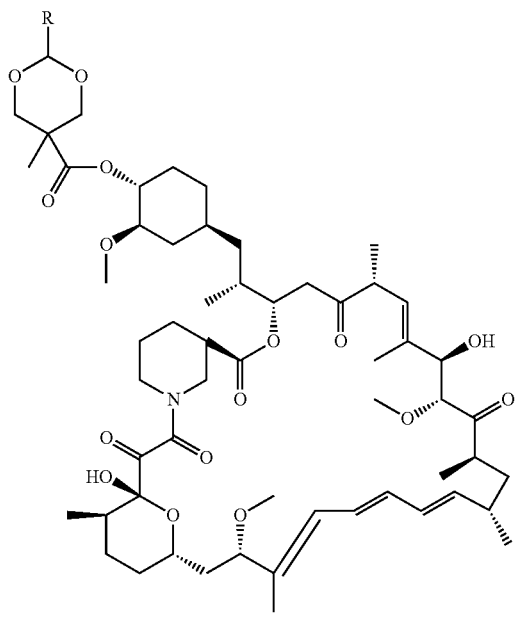

III in which, R represents the same structure as that of the intermediate II; and 3) dissolving the intermediate III in a second organic solvent, adding a dilute sulfuric acid to the second organic solvent to yield a mixed solution; allowing the mixed solution to react at a temperature of between −10 and 20° C. for between 60 and 80 h; adding ethyl acetate and water to the mixed solution, allowing the mixed solution to stand for stratification; separating an aqueous phase from an organic phase; extracting the aqueous phase by ethyl acetate to produce a new organic phase; combining the two organic phases, precipitating and purifying a resulting product by silica gel column chromatography to yield temsirolimus.

In a class of this embodiment, the substituted aromatic aldehyde is selected from the group consisting of benzaldehyde, p-methoxybenzaldehyde, p-chlorobenzaldehyde, and 4-(trifluoromethyl)benzaldehyde. A molar ratio between 2,2-dimethylol propionic acid and the substituted aromatic aldehyde is 1:1. A dosage of p-toluenesulfonic acid is between 10 and 20 wt. % of that of the substituted aromatic aldehyde.

In a class of this embodiment, a molar ratio between rapamicin, the intermediate II, and 2,4,6-trichlorobenzoyl chloride in step 2) is 1:1-1.3:1-1.2. The first organic solvent is selected from the group consisting of toluene, benzene, xylene, ether, methyl tert-butyl ether, tetrahydrofuran, dichloromethane, chloroform, carbon tetrachloride, 1,2-dichloroethane, and ethyl acetate. The alkali is selected from the group consisting of triethylamine, N,N-diisopropylethylamine, and N,N-dimethylaniline. The acid binding agent is selected from the group consisting of pyridine, 4-dimethylaminopyridine (DMAP), 4-pyrrolidinopyridine, and N-methylimidazole.

In a class of this embodiment, a molar ratio between the intermediate III and the dilute sulfuric acid is 1:4-10. The second organic solvent is selected from the group consisting of ether, methyl tert-butyl ether, tetrahydrofuran, methanol, ethanol, isopropanol, tert-butyl alcohol, and acetone.

Advantages of the invention are summarized as follows: the method for synthesizing temsirolimus of the invention employs two-step reactions to yield the product, has a high yield of 54.8%, simplified synthetic steps and thus low production cost.

BRIEF DESCRIPTION OF THE DRAWINGS

The invention is described hereinbelow with reference to the accompanying drawings, in which.

DETAILED DESCRIPTION OF THE EMBODIMENTS

Figure 1:
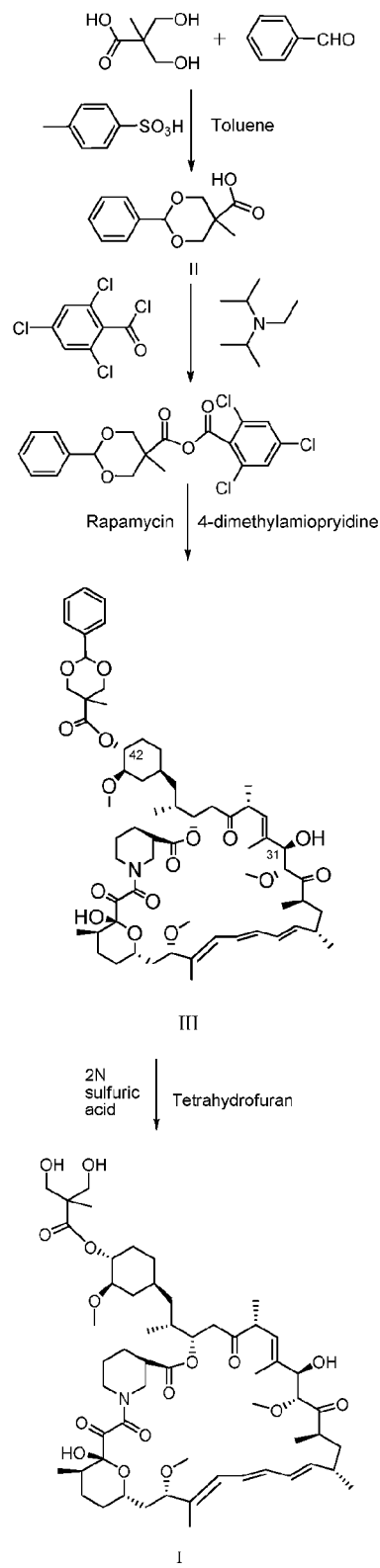
FIG. 1 is a synthetic route for temsirolimus in accordance with one embodiment of the invention.
Figure 2:
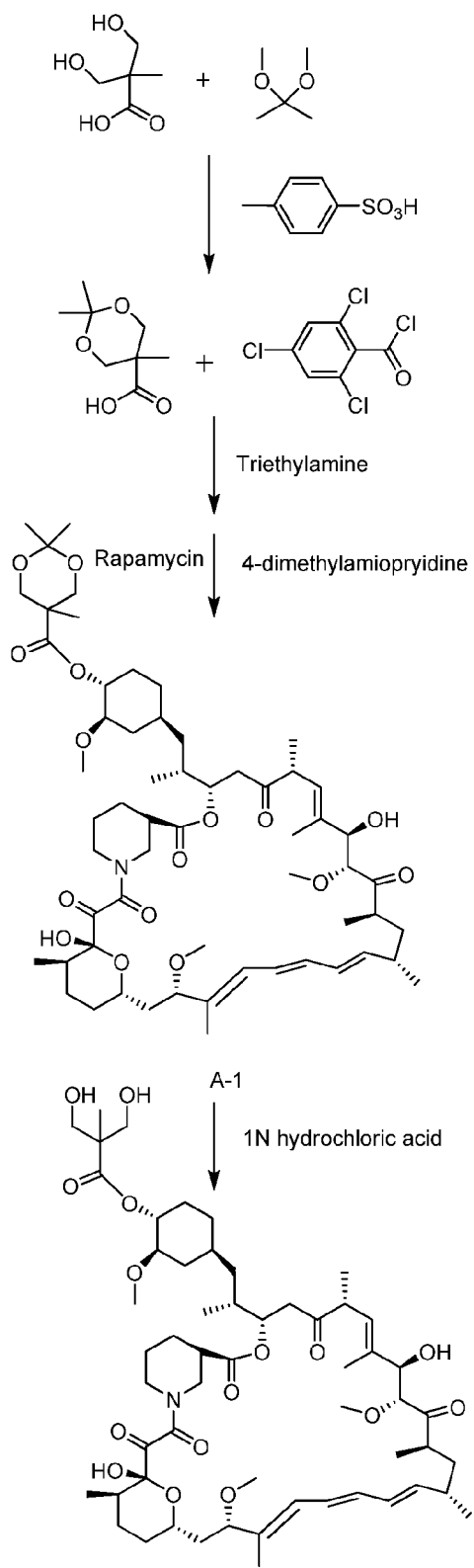
FIG. 2 is a first synthetic route for temsirolimus in the prior art.
Figure 3:
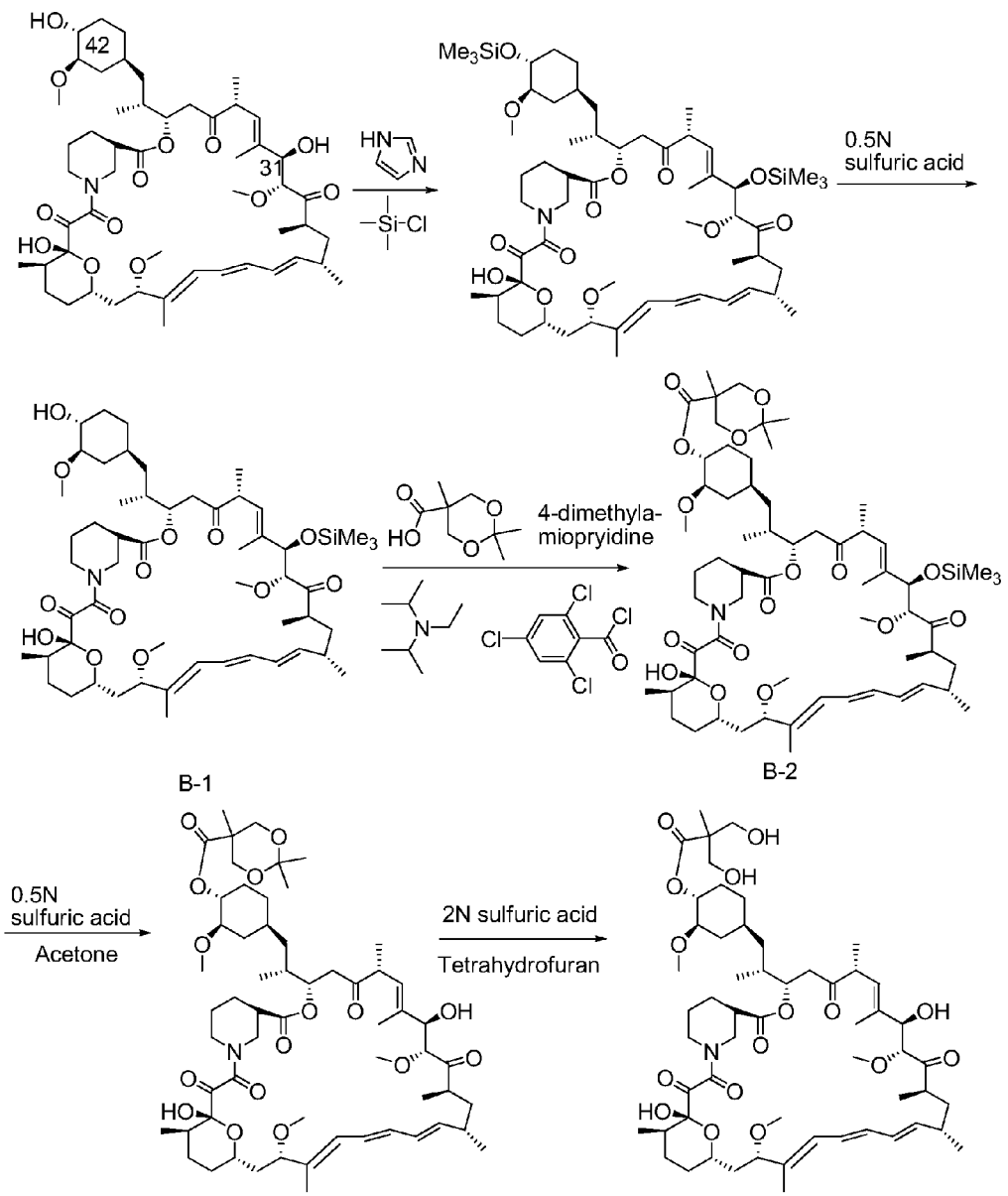
FIG. 3 is a second synthetic route for temsirolimus in the prior art.
Figure 4:
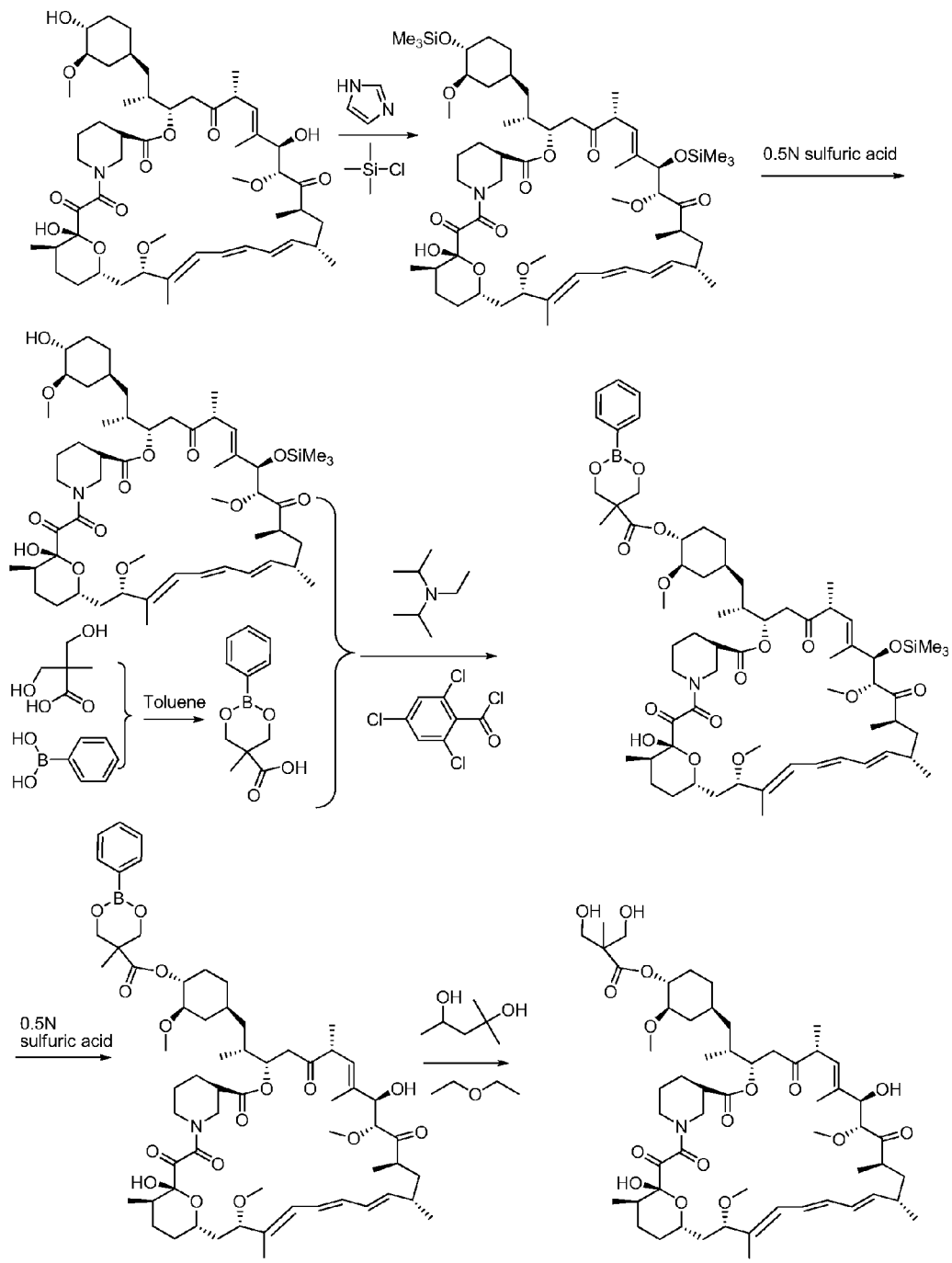
FIG. 4 is a third synthetic route for temsirolimus in the prior art.
Figure 5:
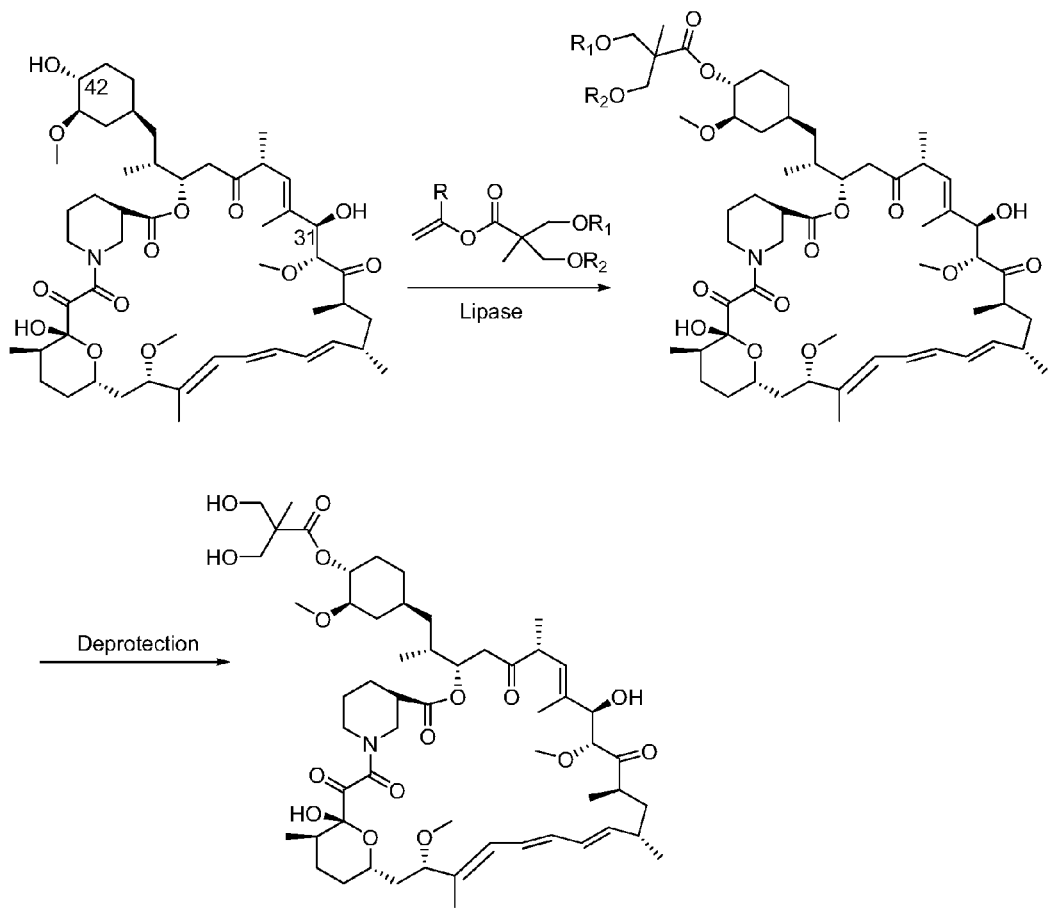
FIG. 5 is a fourth synthetic route for temsirolimus in the prior art.

For further illustrating the invention, experiments detailing a method for preparing temsirolimus are described below. It should be noted that the following examples are intended to describe and not to limit the invention.

EXAMPLE 1

1) To a 100 mL single-mouth bottle 0.80 g (5.9 mmol) of 2,2-dimethylol propionic acid, 0.63 g (5.9 mmol) of benzaldehyde, 0.1 g of p-toluenesulfonic acid, and 40 mL of toluene were added to form a solution. The solution was then heated and refluxed for 8 h. Thereafter, the solution was cooled to room temperature and a product precipitated in a decompression condition. 30 mL of saturated sodium carbonate aqueous solution was added to the solution to from a mixture. After being stirred for 20 min, the mixture was transferred to a separating funnel, and was extracted by using 30 mL×3 of ether whereby separating an aqueous phase from an organic phase. A 2 N sulfuric acid was then added to the aqueous phase to neutralize the pH value thereof. Finally, the aqueous phase was filtrated and dried to a constant weight to yield intermediate II-1, the formula of which is as follows. 1.09 g of the intermediate II-1 was obtained, and the yield thereof was 82.3%.

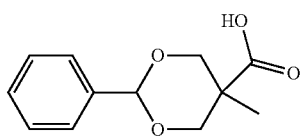

II-1

2) To a 100 mL four-mouth bottle 0.06 g (0.284 mmol) of the intermediate II-1, 6 mL of dichloromethane, 0.06 g (0.438 mmol) of N,N-diisopropylethylamine, and 0.06 g (0.263 mmol) of 2,4,6-trichlorobenzoyl chloride were added to form a reaction solution. The reaction solution was stirred in the presence of nitrogen gas at the temperature of 14° C. for 4 h, and was then cooled to the temperature of −10° C. 0.02 g (0.219 mmol) of rapamycin and 0.05 g (0.438 mmol) of DMAP were added to the reaction solution. Thereafter, the reaction solution was heated to the temperature of 14° C. to react. After the reaction lasted for 14 h, 30 mL of water and 30 mL of ethyl acetate were added to the reaction solution and stirred for 10 min. A resulting mixture was then transferred to the separating funnel to separate an organic phase from an aqueous phase. After that, the organic phase was washed by using the 2N sulfuric solution (10 mL×2), water (10 mL), a 5% sodium bicarbonate aqueous solution (10 mL), and saturated brine (10 mL), respectively, and dried by using anhydrous magnesium sulfate. Finally, a resulting product was filtrated, precipitated, and separated by silica gel column chromatography (between 200 and 300 mesh, an eluent comprising petroleum ether and acetic ether according to a ratio of 1:1) to yield a white solid intermediate III-1. 0.21 g of the white solid intermediate III-1 was obtained, and the yield thereof was 49.0%.

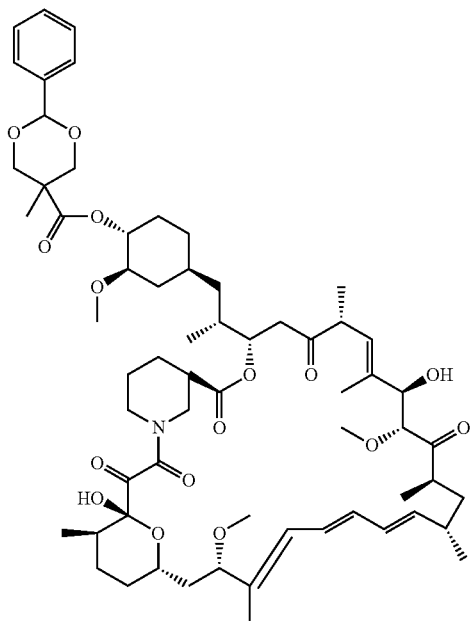

III-1

3) 0.12 g (0.11 mmol) of the intermediate III-1, and 10 mL of tetrahydrofuran were added to a 100 mL single-mouth bottle, respectively, to yield a mixed solution. Then, the mixed solution was cooled to the temperature of 0° C. below, and 0.3 mL (0.6 mmol) of the 2 N sulfuric acid was dropped to the mixed solution. After that, the temperature of the mixed solution was raised to 14° C., and the mixed solution was maintained at such a temperature for 80 h to react. Thereafter, 30 mL of ethyl acetate and 20 mL of water were added to the mixed solution. The mixed solution was stirred for 20 min and then transferred to the separating funnel to separate the organic phase from the aqueous phase. 20 mL×2 of ethyl acetate was used to extract the aqueous phase to produce a new organic phase. Then, the two organic phases were combined, washed respectively by 20 mL of sodium carbonate aqueous solution, 30 mL of water, and 20 mL of saturated brine, and dried by using anhydrous magnesium sulfate. Finally, a resulting organic phase was filtrated, precipitated, and separated by silica gel column chromatography to yield 0.08 g of a white solid temsirolimus, and the yield thereof was 72.7%. MS:[M+Na]$^+$1052.6; $^1$H NMR (CDCl$_3$, 300 MHz): 4.70 (m, 1H), 3.86 (d, 2H), 3.81 (d, 2H), 1.12 (s, 3H).

EXAMPLE 2

1) To a 100 mL single-mouth bottle 0.80 g (5.9 mmol) of 2,2-dimethylol propionic acid, 0.83 g (5.9 mmol) of p-chlorobenzaldehyde, 0.13 g of p-toluenesulfonic acid, and 40 mL of toluene were added to form a solution. The solution was then heated and refluxed for 8 h. Thereafter, the solution was cooled to room temperature and a product precipitated in a decompression condition. 30 mL of saturated sodium carbonate aqueous solution was added to the solution to from a mixture. After being stirred for 20 min, the mixture was transferred to a separating funnel, and was extracted by using 30 mL×3 of ether whereby separating an aqueous phase from an organic phase. A 2 N sulfuric acid was then added to the aqueous phase to neutralize the pH value thereof. Finally, the aqueous phase was filtrated and dried to a constant weight to yield intermediate II-2, the formula of which is as follows. 1.28 g of the intermediate II-2 was obtained, and the yield thereof was 84.3%.

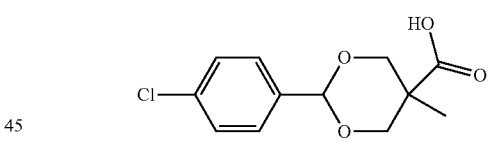

II-2

2) To a 100 mL four-mouth bottle 0.07 g (0.284 mmol) of the intermediate II-2, 6 mL of dichloromethane, 0.06 g (0.438 mmol) of N,N-diisopropylethylamine, and 0.06 g (0.263 mmol) of 2,4,6-trichlorobenzoyl chloride were added to form a reaction solution. The reaction solution was stirred in the presence of nitrogen gas at the temperature of 14° C. for 4 h, and was then cooled to the temperature of −10° C. 0.02 g (0.219 mmol) of rapamycin and 0.05 g (0.438 mmol) of DMAP were added to the reaction solution. Thereafter, the reaction solution was heated to the temperature of 14° C. to react. After the reaction lasted for 14 h, 30 mL of water and 30 mL of ethyl acetate were added to the reaction solution and stirred for 10 min. A resulting mixture was then transferred to the separating funnel to separate an organic phase from an aqueous phase. After that, the organic phase was washed by using the 2N sulfuric solution (10 mL×2), water (10 mL), a 5% sodium bicarbonate aqueous solution (10 mL), and saturated brine (10 mL), respectively, and dried by using anhydrous magnesium sulfate. Finally, a resulting product was filtrated, precipitated, and separated by silica gel column chromatography to yield a white solid intermediate III-2. 0.12 g of the white solid intermediate III-2 was obtained, and the yield thereof was 48.6%.

III-2

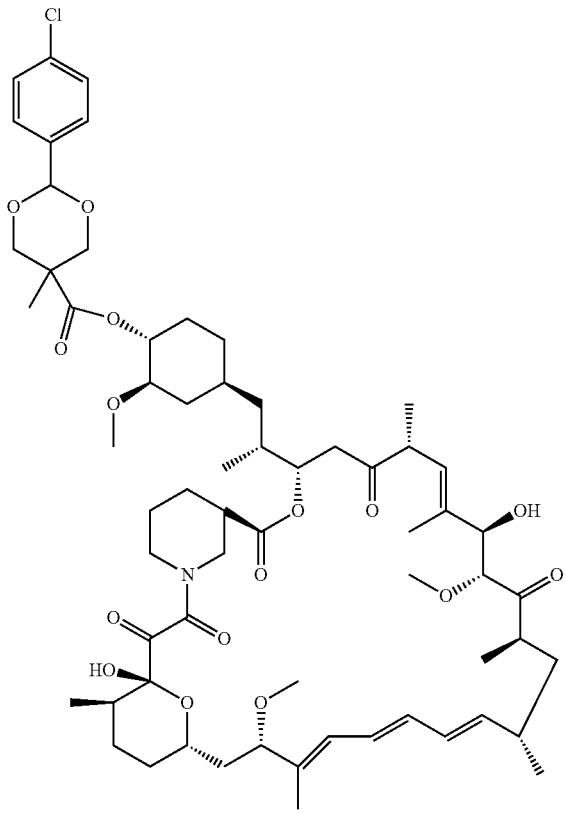

3) 0.12 g (0.10 mmol) of the intermediate III-2, and 10 mL of tetrahydrofuran were added to a 100 mL single-mouth bottle, respectively, to yield a mixed solution. Then, the mixed solution was cooled to the temperature of 0° C. below, and 0.3 mL (0 6 mmol) of the 2 N diluted sulfuric acid was dropped to the mixed solution. After that, the temperature of the mixed solution was raised to 14° C., and the mixed solution was maintained at such a temperature for 80 h to react. Thereafter, 30 mL of ethyl acetate and 20 mL of water were added to the mixed solution. The mixed solution was stirred for 20 min and then transferred to the separating funnel to separate the organic phase from the aqueous phase. 20 mL×2 of ethyl acetate was used to extract the aqueous phase to produce a new organic phase. Then, the two organic phases were combined, washed respectively by 20 mL of sodium carbonate aqueous solution, 30 mL of water, and 20 mL of saturated brine, and dried by using anhydrous magnesium sulfate. Finally, a resulting organic phase was filtrated, precipitated, and separated by silica gel column chromatography to yield a white solid temsirolimus. 0.08 g of white solid temsirolimus was obtained, and the yield thereof was 71.5%.

EXAMPLE 3

To a 100 mL four-mouth bottle 0.06 g (0.284 mmol) of the intermediate II-1 obtained from Example 1, 6 mL of dichloromethane, 0.04 g (0.438 mmol) of triethylamine, and 0.06 g (0.263 mmol) of 2,4,6-trichlorobenzoyl chloride were added to form a reaction solution. The reaction solution was stirred in the presence of nitrogen gas at the temperature of 14° C. for 4 h, and was then cooled to the temperature of –10° C. 0.02 g (0.219 mmol) of rapamycin and 0.05 g (0.438 mmol) of DMAP were added to the reaction solution. Thereafter, the reaction solution was heated to the temperature of 14° C. to react. After the reaction lasted for 14 h, 30 mL of water and 30 mL of ethyl acetate were added to the reaction solution and stirred for 10 min. A resulting mixture was then transferred to the separating funnel to separate an organic phase from an aqueous phase. After that, the organic phase was washed by using a 2N sulfuric solution (10 mL×2), water (10 mL), a 5% sodium bicarbonate aqueous solution (10 mL), and saturated brine (10 mL), respectively, and dried by using anhydrous magnesium sulfate. Finally, a resulting product was filtrated, precipitated, and separated by silica gel column chromatography (between 200 and 300 mesh, an eluent comprising petroleum ether and acetic ether according to a ratio of 1:1) to yield a white solid intermediate III-1. 0.11 g of the white solid intermediate III-1 was obtained, and the yield thereof was 44.0%.

EXAMPLE 4

To a 100 mL four-mouth bottle 0.06 g (0.284 mmol) of the intermediate II-1 obtained from Example 1, 6 mL of dichloromethane, 0.06 g (0.438 mmol) of N,N-diisopropylethylamine, and 0.06 g (0.263 mmol) of 2,4,6-trichlorobenzoyl chloride were added to form a reaction solution. The reaction solution was stirred in the presence of nitrogen gas at the temperature of 14° C. for 4 h, and was then cooled to the temperature of –10° C. 0.02 g (0.219 mmol) of rapamycin and 0.04 g (0.438 mmol) of pyridine were added to the reaction solution. Thereafter, the reaction solution was heated to the temperature of 14° C. to react. After the reaction lasted for 14 h, 30 mL of water and 30 mL of ethyl acetate were added to the reaction solution and stirred for 10 min. A resulting mixture was then transferred to the separating funnel to separate an organic phase from an aqueous phase. After that, the organic phase was washed by using a 2N sulfuric solution (10 mL×2), water (10 mL), a 5% sodium bicarbonate aqueous solution (10 mL), and saturated brine (10 mL), respectively, and dried by using anhydrous magnesium sulfate. Finally, a resulting product was filtrated, precipitated, and separated by silica gel column chromatography (between 200 and 300 mesh, an eluent comprising petroleum ether and acetic ether according to a ratio of 1:1) to yield a white solid intermediate III-1. 0.10 g of the white solid intermediate III-1 was obtained, and the yield thereof was 40.0%.

EXAMPLE 5

0.12 g (0.10 mmol) of the intermediate III-1 obtained from Example 1, and 10 mL of tetrahydrofuran were added to a 100 mL single-mouth bottle, respectively, to yield a mixed solution. Then, the mixed solution was cooled to the temperature of 0° C. below, and 0.4 mL (0.88 mmol) of a 2 N sulfuric acid was dropped to the mixed solution. After that, the temperature of the mixed solution was raised to 14° C., and the mixed solution was maintained at such a temperature for 68 h to react. Thereafter, 30 mL of ethyl acetate and 20 mL of water were added to the mixed solution. The mixed solution was stirred for 20 min and then transferred to the separating funnel to separate the organic phase from the aqueous phase. 20 mL×2 of ethyl acetate was used to extract the aqueous phase to produce a new organic phase. Then, the two organic phases were combined, washed respectively by 20 mL of sodium carbonate aqueous solution, 30 mL of water, and 20 mL of saturated brine, and dried by using anhydrous magnesium sulfate. Finally, a resulting organic phase was filtrated, precipitated, and separated by silica gel column chromatography to yield a white solid temsirolimus. 0.07 g of white solid temsirolimus was obtained, and the yield thereof was 70.0%.

EXAMPLE 6

0.12 g (0.10 mmol) of the intermediate III-1 obtained from Example 1, and 10 mL of acetone were added to a 100 mL single-mouth bottle, respectively, to yield a mixed solution. Then, the mixed solution was cooled to the temperature of 0° C. below, and 0.4 mL (0.8 mmol) of a 2 N sulfuric acid was dropped to the mixed solution. After that, the temperature of the mixed solution was raised to 14° C., and the mixed solution was maintained at such a temperature for 68 h to react. Thereafter, 30 mL of ethyl acetate and 20 mL of water were added to the mixed solution. The mixed solution was stirred for 20 min and then transferred to the separating funnel to separate the organic phase from the aqueous phase. 20 mL×2 of ethyl acetate was used to extract the aqueous phase to produce a new organic phase. Then, the two organic phases were combined, washed respectively by 20 mL of sodium carbonate aqueous solution, 30 mL of water, and 20 mL of saturated brine, and dried by using anhydrous magnesium sulfate. Finally, a resulting organic phase was filtrated, precipitated, and separated by silica gel column chromatography to yield a white solid temsirolimus. 0.07 g of white solid temsirolimus was obtained, and the yield thereof was 70.0%.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:
1. A method for preparing a compound of formula I,

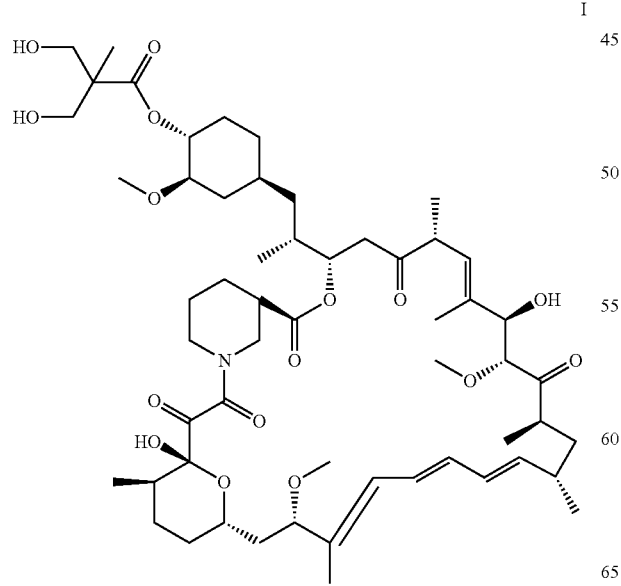

and the method comprising:

1) preparing a solution comprising: a raw material comprising 2,2-dimethylol propionic acid and a substituted aromatic aldehyde, a catalyst comprising p-toluenesulfonic acid, and a solvent comprising methylbenzene; heating and refluxing the solution for 8 h; precipitating a product; adding a saturated sodium carbonate aqueous solution and ether to the solution; allowing a resulting mixture to stand for stratification; separating an aqueous phase from an organic phase; adjusting pH value of the aqueous phase to be neutral; filtrating, and drying the aqueous phase to yield intermediate II represented by the following formula:

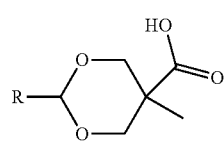

wherein, R represents

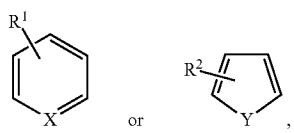

X represents a carbon atom or nitrogen atom;

$R^1$ represents a hydrogen atom, between one and five $C_1$-$C_6$ alkyls, between one and five $C_1$-$C_6$ alkoxys, between one and five $C_1$-$C_6$ alkenyls, between one and five $C_1$-$C_6$ alkynyls, between one and five hydroxyls, one or two methylenedioxys (OCH$_2$O), one or two ethylenedioxys (OCH$_2$CH$_2$O), between one and five halogen atoms, between one and five nitryls, between one and five trifluoromethyls, or between one and five trifluoromethoxys;

Y represents nitrogen atom, oxygen atom, or sulfur atom; and $R^2$ represents hydrogen atom, between one and four $C_1$-$C_6$ alkyls, between one and four $C_1$-$C_6$ alkoxys, between one and four $C_1$-$C_6$ alkenyls, between one and four $C_1$-$C_6$ alkynyls, between one and four hydroxyls, between one and four halogen atoms, between one and four nitryls, between one and four trifluoromethyls, or between one and four trifluoromethoxys;

2) dissolving the intermediate II, an alkali, and 2,4,6-trichlorobenzoyl chloride, in a first organic solvent to form a mixture; allowing the mixture to react in the presence of nitrogen gas at a temperature of between −20 and 40° C. for between 4 and 5 h; adjusting the temperature of the mixture to −10° C.; adding rapamycin and an acid binding agent to the mixture, allowing the mixture to react overnight at room temperature; and separating a product by silica gel column chromatography to yield intermediate III represented by the following formula:

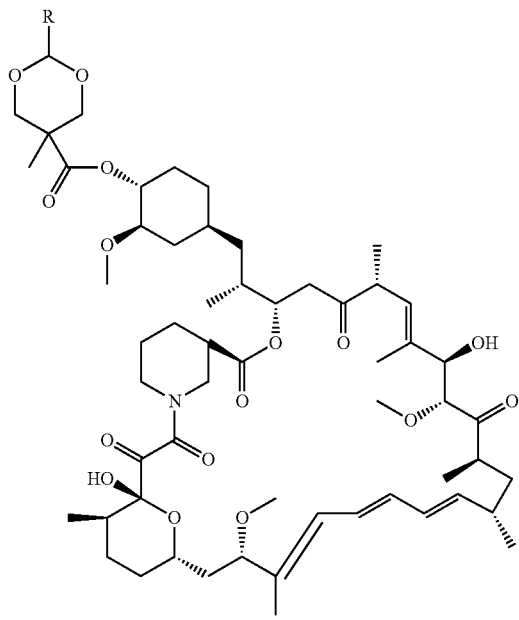

wherein, R represents the same structure as that of the intermediate II; and 3) dissolving the intermediate III in a second organic solvent, adding a dilute sulfuric acid to the second organic solvent to yield a mixed solution; allowing the mixed solution to react at a temperature of between −10 and 20° C. for between 60 and 80 h; adding ethyl acetate and water to the mixed solution, allowing the mixed solution to stand for stratification; separating an aqueous phase from an organic phase; extracting the aqueous phase by ethyl acetate to produce a new organic phase; combining the two organic phases, precipitating and purifying a resulting product by silica gel column chromatography to yield the compound.

2. The method of claim 1, wherein
the substituted aromatic aldehyde is selected from the group consisting of benzaldehyde, p-methoxybenzaldehyde, p-chlorobenzaldehyde, and 4-(trifluoromethyl) benzaldehyde;
a molar ratio between 2,2-dimethylol propionic acid and the substituted aromatic aldehyde is 1:1; and
a dosage of p-toluenesulfonic acid is between 10 and 20 wt. % of that of the substituted aromatic aldehyde.

3. The method of claim 1, wherein
a molar ratio between rapamicin, the intermediate II, and 2,4,6-trichlorobenzoyl chloride in step 2) is 1:1-1.3:1-1.2;
the first organic solvent is selected from the group consisting of toluene, benzene, xylene, ether, methyl tert-butyl ether, tetrahydrofuran, dichloromethane, chloroform, carbon tetrachloride, 1,2-dichloroethane, and ethyl acetate;
the alkali is selected from the group consisting of triethylamine, N,N-diisopropylethylamine, and N,N-dimethylaniline; and
the acid binding agent is selected from the group consisting of pyridine, 4-dimethylaminopyridine (DMAP), 4-pyrrolidinopyridine, and N-methylimidazole.

4. The method of claim 1, wherein
a molar ratio between the intermediate III and the dilute sulfuric acid is 1:4-10; and
the second organic solvent is selected from the group consisting of ether, methyl tert-butyl ether, tetrahydrofuran, methanol, ethanol, isopropanol, tert-butyl alcohol, and acetone.

* * * * *